United States Patent [19]

Yokokoji et al.

[11] Patent Number: 5,621,147

[45] Date of Patent: Apr. 15, 1997

[54] TRIFLUORO-2-(TRANS-4-SUBSTITUTED CYCLOHEXYL) ETHYLENES AND PROCESS FOR THEIR PRODUCTION

[75] Inventors: Osamu Yokokoji; Tamaki Simizu; Seisaku Kumai, all of Yokohama, Japan

[73] Assignee: Asahi Glass Company Ltd., Tokyo, Japan

[21] Appl. No.: 433,967

[22] Filed: May 4, 1995

[30] Foreign Application Priority Data

Jun. 24, 1994 [JP] Japan .................................. 6-143480

[51] Int. Cl.⁶ .......................... C07C 22/00; C07C 43/188; C07C 43/192; C07C 17/25
[52] U.S. Cl. .......................... 568/669; 544/242; 546/192; 549/22; 549/369; 558/425; 570/128; 570/130; 570/131; 570/144; 570/155; 570/156; 570/157; 570/158
[58] Field of Search ................... 570/128, 130, 570/131, 144, 155–158; 568/669, 425; 549/22, 369; 546/192; 544/242

[56] References Cited

U.S. PATENT DOCUMENTS

| | | | |
|---|---|---|---|
| 2,612,528 | 9/1952 | Cohen | 570/128 |
| 2,651,627 | 9/1953 | Prober | 570/128 |
| 2,808,425 | 10/1957 | Haszeldine | 570/128 |
| 2,945,896 | 7/1960 | Tarrant et al. | 570/156 |
| 4,877,548 | 10/1989 | Kitano et al. | 570/128 |
| 5,396,000 | 3/1995 | Nappa et al. | 570/156 |
| 5,458,806 | 10/1995 | Bartmann et al. | 570/144 |

FOREIGN PATENT DOCUMENTS

| | | |
|---|---|---|
| 0325796 | 8/1989 | European Pat. Off. . |
| 0377469 | 7/1990 | European Pat. Off. . |
| 0560382 | 9/1993 | European Pat. Off. . |
| 593997 | 4/1994 | European Pat. Off. ............... 570/128 |
| 4023107 | 1/1992 | Germany ............................. 568/669 |
| WO92/21734 | 12/1992 | WIPO . |

*Primary Examiner*—Joseph E. Evans
*Attorney, Agent, or Firm*—Oblon, Spivak, McClelland, Maier & Neustadt, P.C.

[57] ABSTRACT

A 1,1,2-trifluoro-2-(trans-4-substituted cyclohexyl)ethylene of the formula (1):

$$R-(A)_m-Cy-CF=CF_2 \qquad (1)$$

wherein R is a $C_{1-10}$ alkyl group, a halogen atom or a cyano group, provided that in the case of the alkyl group, an oxygen atom may be interposed in a carbon-carbon bond of the alkyl group or in a carbon-carbon bond between this alkyl group and A, some of carbon-carbon bonds in the alkyl group may be triple bonds or double bonds, one $-CH_2-$ group in the alkyl group may be substituted by a carbonyl group, and some or all of hydrogen atoms in the alkyl group may be substituted by fluorine atoms;

Cy is an unsubstituted trans-1,4-cyclohexylene group;

A is a trans-1,4-cyclohexylene group, a 1,4-phenylene group or a 1,4-cyclohexenylene group, wherein each of such cyclic groups is unsubstituted or substituted by one or more halogen atoms or cyano groups, one or more =CH— groups constituting rings of such cyclic groups may be substituted by nitrogen atoms, and one or more $-CH_2-$ groups constituting rings of such cyclic groups may be substituted by oxygen atoms or sulfur atoms; and m is 0 or 1.

10 Claims, No Drawings

TRIFLUORO-2-(TRANS-4-SUBSTITUTED CYCLOHEXYL) ETHYLENES AND PROCESS FOR THEIR PRODUCTION

The present invention relates to 1,1,2-trifluoro-2-(trans-4-substituted cyclohexyl)ethylenes useful as intermediates for liquid crystal compounds and a process for their production.

The 1,1,2-trifluoro-2-(trans-4-substituted cyclohexyl)ethylenes of the present invention are novel compounds. A known compound having a structure similar to the compounds of the present invention may be 1,1,2-trifluoro-2-butylethylene. This known compound can be obtained in a yield of 80% by reacting tetrafluoroethylene with n-butyl lithium (J. Chem. Soc., 1956, 400 (1956)).

However, to prepare a 1,1,2-trifluoro-2-(trans-4-alkylcyclohexyl)ethylene of the present invention by adopting such a known method, it is necessary to obtain a trans-4-alkylcyclohexyl lithium first. However, a 4-alkylcyclohexyl lithium of trans-form can hardly be synthesized. Besides, it is practically difficult to have the actual reaction proceeded while maintaining the stereochemical structure.

It is an object of the present invention to provide novel compounds useful as intermediates for liquid crystals and a process for efficiently producing such novel compounds.

The present invention provides a 1,1,2-trifluoro-2-(trans-4-substituted cyclohexyl)ethylene of the formula (1):

$$R—(A)_m—Cy—CF=CF_2 \quad (1)$$

wherein R is a $C_{1-10}$ alkyl group, a halogen atom or a cyano group, provided that in the case of the alkyl group, an oxygen atom may be interposed in a carbon-carbon bond of the alkyl group or in a carbon-carbon bond between this alkyl group and A, some of carbon-carbon bonds in the alkyl group may be triple bonds or double bonds, one —$CH_2$— group in the alkyl group may be substituted by a carbonyl group, and some or all of hydrogen atoms in the alkyl group may be substituted by fluorine atoms;

Cy is an unsubstituted trans-1,4-cyclohexylene group;

A is a trans-1,4-cyclohexylene group, a 1,4-phenylene group or a 1,4-cyclohexenylene group, wherein each of such cyclic groups is unsubstituted or substituted by one or more halogen atoms or cyano groups, one or more =CH— groups constituting rings of such cyclic groups may be substituted by nitrogen atoms, and one or more —$CH_2$— groups constituting rings of such cyclic groups may be substituted by oxygen atoms or sulfur atoms; and m is 0 or 1.

Further, the present invention provides a process for producing a 1,1,2-trifluoro-2-(trans-4-substituted cyclohexyl)ethylene of the formula (1), which comprises fluorinating a compound of the formula (13) to obtain a compound of the formula (14), and further dehydrofluorinating the compound of the formula (14):

$$R—(A)_m—Cy—CH=CF_2 \quad (13)$$

$$R—(A)_m—Cy—CHFCF_3 \quad (14)$$

$$R—(A)_m—Cy—CF=CF2 \quad (1)$$

wherein R, Cy, A and m are as defined above.

Now, the present invention will be described in detail with reference to the preferred embodiments.

R in the formula (1) is a $C_{1-10}$ alkyl group, a halogen atom or a cyano group, preferably a $C_{1-10}$ alkyl group. The carbon number of the alkyl group is preferably from 1 to 8, more preferably from 1 to 6. In the case of the alkyl group, an oxygen atom may be interposed between a carbon-carbon bond in the alkyl group or in a carbon-carbon bond between the alkyl group and A. Further, some of carbon-carbon bonds in the alkyl group may be in the form of triple bonds or double bonds, and one —$CH_2$— group in the alkyl group may be substituted by a carbonyl group. The group wherein an oxygen atom is interposed in a carbon-carbon bond in the alkyl group or in a carbon-carbon bond between the alkyl group and A, is preferably a group wherein one oxygen atom is interposed, i.e. an alkoxyl group or a group having an alkoxyl moiety. The group wherein some of carbon-carbon bonds in the alkyl group are triple bonds or double bonds, is preferably a group wherein one carbon-carbon bond is a triple bond or a double bond, i.e. an alkenyl group or an alkynyl group. The group wherein one —$CH_2$— group in the alkyl group is substituted by a carbonyl group, is preferably an acyl group.

Further, some or all of hydrogen atoms of such an alkyl group (i.e. an alkyl group, a group wherein an oxygen atom is interposed in a carbon-carbon bond in the alkyl group or in a carbon-carbon bond between the alkyl group and A, a group wherein some of carbon-carbon bonds in the alkyl group are triple bonds or double bonds, or a group wherein one —$CH_2$— group in the alkyl group is substituted by a carbonyl group) may be substituted by fluorine atoms. Particularly preferred is a group wherein all of the hydrogen atoms are substituted by fluorine atoms, or a group having a moiety wherein all of hydrogen atoms are substituted by fluorine atoms.

Further, R is preferably of a straight chain structure in any one of the above alkyl groups.

In a case where R in the formula (1) is a halogen atom, a fluorine atom or a chlorine atom is preferred, and particularly preferred is a fluorine atom. Further, Cy in the formula (1) is an unsubstituted trans-1,4-cyclohexylene group.

A in the formula (1) is a trans-1,4-cyclohexylene group, a 1,4-phenylene group or a 1,4-cyclohexenylene group. Each of such cyclic groups is unsubstituted or substituted by one or more halogen atoms or cyano groups. When A has a substituent, the substituent is preferably a halogen atom, particularly a fluorine atom or a chlorine atom.

Further, one or more =CH— groups constituting rings of such cyclic groups of A may be substituted by nitrogen atoms, and one or more —$CH_2$— groups constituting such rings may be substituted by oxygen atoms or sulfur atoms. However, the =CH— groups and the —$CH_2$— groups constituting the rings are preferably unsubstituted.

In the formula (1), m is 0 or 1. When m is 0, Cy and R in the formula (1) are directly bonded.

The 1,1,2-trifluoro-2-(trans-4-substituted cyclohexyl)ethylene of the above formula (1) is preferably the one represented by the formula (2):

$$R^1—(A^1)_m—Cy—CF=CF_2 \quad (2)$$

In the formula (2), Cy and m have the same meanings as in the formula (1), and $R^1$ and $A^1$ have the following meanings.

$R^1$ is a $C_{1-10}$ alkyl group, wherein an oxygen atom may be interposed in a carbon-carbon bond of the alkyl group or in a carbon-carbon bond between the alkyl group and $A^1$, some of carbon-carbon bonds in the alkyl group may be triple bonds or double bonds, one —$CH_2$— group in the alkyl group may be substituted by a carbonyl group, and some or all of hydrogen atoms in such an alkyl group may be substituted by fluorine atoms.

$A^1$ is a trans-1,4-cyclohexylene group, a 1,4-phenylene group or a 1,4-cyclohexenylene group, wherein each of such cyclic groups is unsubstituted or substituted by one or more fluorine atoms.

When m is 0, the formula (2) represents a 1,1,2-trifluoro-2-(trans-4-alkylcyclohexyl)ethylene of the formula (3).

$$R^1-Cy-CF=CF_2 \qquad (3)$$

In the formula (3), $R^1$ and Cy have the same meanings as in the formula (2).

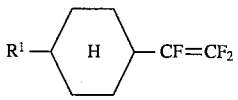
(3)

Specific examples of the compound of the formula (3) include the following compounds. However, the compound of the formula (3) is not limited to such specific examples.

| | |
|---|---|
| C2H$_5$—Cy—CF=CF$_2$ | (3A) |
| n—C$_3$H$_7$—Cy—CF=CF$_2$ | (3B) |
| n—C$_4$H$_9$—Cy—CF=CF$_2$ | (3C) |
| n—C$_5$H$_{11}$—Cy—CF=CF$_2$ | (3D) |
| C$_2$H$_5$O—Cy—CF=CF$_2$ | (3E) |
| C$_2$H$_5$OCH$_2$—Cy—CF=CF$_2$ | (3F) |
| CH$_3$CH=CHCH$_2$—Cy—CF=CF$_2$ | (3G) |
| CH$_3$C≡C—Cy—CF=CF$_2$ | (3H) |
| CF$_3$—Cy—CF=CF$_2$ | (3I) |
| CF$_3$O—Cy—CF=CF2 | (3J) |
| CF$_3$CH$_2$O—Cy—CF=CF$_2$ | (3K) |
| CH$_3$C(O)—Cy—CF=CF$_2$ | (3L) |

Further, when m is 1, the formula (2) represents a compound of the formula (4).

$$R^1-A^1-Cy-CF=CF_2 \qquad (4)$$

In the formula (4), $R^1$, $A^1$ and Cy have the same meanings as in the formula (2).

$A^1$ in the formula (4) is preferably an unsubstituted trans-1,4-cyclohexylene group, an unsubstituted 1,4-phenylene group or an unsubstituted 1,4-cyclohexenylene group, or a 1,4-phenylene group having one or more fluorine atoms.

When $A^1$ is an unsubstituted trans-1,4-cyclohexylene group, the formula (4) represents a 1,1,2-trifluoro-2-[trans-4-(trans-4-alkylcyclohexyl)cyclohexyl]ethylene of the formula (5):

$$R^1-Cy^1-Cy-CF=CF_2 \qquad (5)$$

In the formula (5), $R^1$ and Cy have the same meanings as in the formula (2), and $Cy^1$ is an unsubstituted trans-1,4-cyclohexylene group.

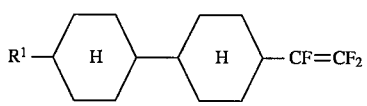
(5)

Specific examples of the compound of the formula (5) include the following compounds. However, the compound of the formula (5) is not limited to such specific examples.

| | |
|---|---|
| C$_2$H$_5$—Cy—Cy—CF=CF$_2$ | (5A) |
| n—C$_3$H$_7$—Cy—Cy—CF=CF$_2$ | (5B) |
| n—C$_4$H$_9$—Cy—Cy—CF=CF$_2$ | (5C) |
| n—C$_5$H$_{11}$—Cy—Cy—CF=CF$_2$ | (5D) |
| C$_2$H$_5$O—Cy—Cy—CF=CF$_2$ | (5E) |
| C$_2$H$_5$OCH$_2$—Cy—Cy—CF=CF$_2$ | (5F) |
| CH$_3$CH=CHCH$_2$—Cy—Cy—CF=CF$_2$ | (5G) |
| CH$_3$C≡C—Cy—Cy—CF=CF$_2$ | (5H) |
| CF$_3$—Cy—Cy—CF=CF$_2$ | (5I) |
| CF$_3$O—Cy—Cy—CF=CF$_2$ | (5J) |
| CF$_3$CH$_2$O—Cy—Cy—CF=CF$_2$ | (5K) |
| CH$_3$C(O)—Cy—Cy—CF=CF$_2$ | (5L) |

Further, when $A^1$ is an unsubstituted 1,4-phenylene group, the formula (4) represents a 1,1,2-trifluoro-2-[trans-4-(4-alkylphenyl)cyclohexyl]ethylene of the formula (6):

$$R^1-Ph-Cy-CF=CF_2 \qquad (6)$$

In the formula (6), $R^1$ and Cy have the same meanings as in the formula (2), and Ph is an unsubstituted 1,4-phenylene group.

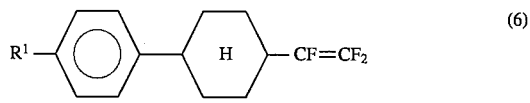
(6)

Specific examples of the compound of the formula (6) include the following compounds. However, the compound of the formula (6) is not limited to such specific examples.

| | |
|---|---|
| C$_2$H$_5$—Ph—Cy—CF=CF$_2$ | (6A) |
| n—C$_3$H$_7$—Ph—Cy—CF=CF$_2$ | (6B) |
| n—C$_4$H$_9$—Ph—Cy—CF=CF$_2$ | (6C) |
| n—C$_5$H$_{11}$—Ph—Cy—CF=CF$_2$ | (6D) |
| C$_2$H$_5$O—Ph—Cy—CF=CF$_2$ | (6E) |
| C$_2$H$_5$OCH$_2$—Ph—Cy—CF=CF$_2$ | (6F) |
| CH$_3$CH=CHCH$_2$—Ph—Cy—CF=CF$_2$ | (6G) |
| CH$_3$C≡C—Ph—Cy—CF=CF$_2$ | (6H) |
| CF$_3$—Ph—Cy—CF=CF$_2$ | (6I) |
| CF$_3$O—Ph—Cy—CF=CF$_2$ | (6J) |
| CF$_3$CH$_2$O—Ph—Cy—CF=CF$_2$ | (6K) |
| CH$_3$C(O)—Ph—Cy—CF=CF$_2$ | (6L) |

Further, when $A^1$ is a 1,4-phenylene group substituted by one fluorine atom, the formula (4) represents a 1,1,2-trifluoro-2-{trans-4-[4-alkyl(fluorophenyl)]cyclohexyl}-ethylene of the formula (7):

$$R^1-PhF-Cy-CF=CF_2 \qquad (7)$$

In the formula (7), $R^1$ and Cy have the same meanings as in the formula (2), PhF is a fluorinated 1,4-di-substituted phenylene group having one hydrogen atom of the 1,4-di-substituted phenylene group substituted by a fluorine atom, wherein the fluorine atom may be bonded to the 2-position (the formula (7-1)) or to the 3-position (the formula (7-2)).

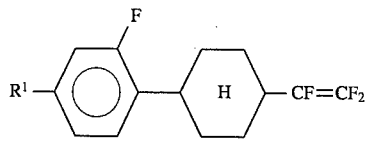 (7-1)

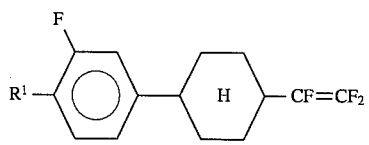 (7-2)

Specific examples of the compound of the formula (7) include the following compounds. However, the compound of the formula (7) is not limited to such specific examples.

| | |
|---|---|
| $C_2H_5$—PhF—Cy—CF=CF$_2$ | (7A) |
| n—$C_3H_7$—PhF—Cy—CF=CF$_2$ | (7B) |
| n—$C_4H_9$—PhF—Cy—CF=CF$_2$ | (7C) |
| n—$C_5H_{11}$—PhF—Cy—CF=CF$_2$ | (7D) |
| $C_2H_5O$—PhF—Cy—CF=CF$_2$ | (7E) |
| $C_2H_5OCH_2$—PhF—Cy—CF=CF$_2$ | (7F) |
| $CH_3CH=CHCH_2$—PhF—Cy—CF=CF | (7G) |
| $CH_3C\equiv C$—PhF—Cy—CF=CF$_2$ | (7H) |
| $CF_3$—PhF—Cy—CF=CF$_2$ | (7I) |
| $CF_3O$—PhF—Cy—CF=CF$_2$ | (7J) |
| $CF_3CH_2O$—PhF—Cy—CF=CF$_2$ | (7K) |
| $CH_3C(O)$—PhF—Cy—CF=CF$_2$ | (7L) |

Further, when $A^1$ is a 1,4-phenylene group substituted by two fluorine atoms, the formula (4) represents a 1,1,2-trifluoro-2-{trans-4-[4-alkyl(difluorophenyl)] cyclohexyl}ethylene of the formula (8):

$R^1$—PhFF—Cy—CF=CF$_2$ (8)

In the formula (8), $R^1$ and Cy have the same meanings as in the formula (2), PhFF is a difluoro-1,4-phenylene group having two hydrogen atoms of the 1,4-di-substituted phenylene group substituted by fluorine atoms, wherein the fluorine atoms may be bonded to the 2- and 3-positions (the formula (8-1)) or to the 3- and 5-positions (the formula (8-2)).

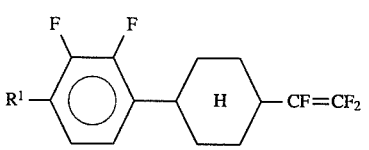 (8-1)

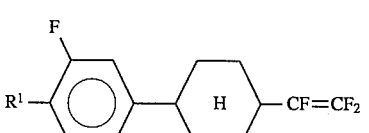 (8-2)

Specific examples of the compound of the formula (8) include the following compounds. However, the compound of the formula (8) is not limited to such specific examples.

| | |
|---|---|
| $C_2H_5$—PhFF—Cy—CF=CF$_2$ | (8A) |
| n—$C_3H_7$—PhFF—Cy—CF=CF$_2$ | (8B) |
| n—$C_4H_9$—PhFF—Cy—CF=CF$_2$ | (8C) |
| n—$C_5H_{11}$—PhFF—Cy—CF=CF$_2$ | (8D) |
| $C_2H_5O$—PhFF—Cy—CF=CF$_2$ | (8E) |
| $C_2H_5OCH_2$—PhFF—Cy—CF=CF$_2$ | (8F) |
| $CH_3CH=CHCH_2$—PhFF—Cy—CF=CF | (8G) |
| $CH_3C\equiv C$—PhFF—Cy—CF=CF$_2$ | (8H) |
| $CF_3$—PhFF—Cy—CF=CF$_2$ | (8I) |
| $CF_3O$—PhFF—Cy—CF=CF$_2$ | (8J) |
| $CF_3CH_2O$—PhFF—Cy—CF=CF$_2$ | (8K) |
| $CH_3C(O)$—PhFF—Cy—CF=CF$_2$ | (8L) |

Further, when $A^1$ is an unsubstituted 1,4-cyclohexenylene group, the formula (4) represents a 1,1,2-trifluoro-2-[trans-4-(4-alkylcyclohexenyl)cyclohexyl]ethylene of the formula (9):

$R^1$—Ch—Cy—CF=CF$_2$ (9)

In the formula (9), $R^1$ and Cy have the same meanings as in the formula (2), and Ch is a 1,4-cyclohexenylene group, preferably a 1,4-cyclohexylen-1-yl group. When Ch is a 1,4-cyclohexylen-1-yl group, the formula (9) represents a compound of the formula (9-1).

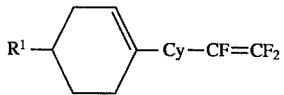 (9-1)

Specific examples of the compound of the formula (9) include the following compounds. However, the compound of the formula (9) is not limited to such specific examples.

| | |
|---|---|
| $C_2H_5$—Ch—Cy—CF=CF$_2$ | (9A) |
| n—$C_3H_7$—Ch—Cy—CF=CF$_2$ | (9B) |
| n—$C_4H_9$—Ch—Cy—CF=CF$_2$ | (9C) |
| n—$C_5H_{11}$—Ch—Cy—CF=CF$_2$ | (9D) |
| $C_2H_5O$—Ch—Cy—CF=CF$_2$ | (9E) |
| $C_2H_5OCH_2$—Ch—Cy—CF=CF$_2$ | (9F) |
| $CH_3CH=CHCH_2$—Ch—Cy—CF=CF$_2$ | (9G) |
| $CH_3C\equiv C$—Ch—Cy—CF=CF$_2$ | (9H) |
| $CF_3$—Ch—Cy—CF=CF$_2$ | (9I) |
| $CF_3$—Ch—Cy—CF=CF$_2$ | (9J) |
| $CF_3CH_2O$—Ch—Cy—CF=CF$_2$ | (9K) |
| $CH_3C(O)$—Ch—Cy—CF=CF$_2$ | (9L) |

Further, specific examples of the compound of the formula (1) wherein A is a group substituted by one or more cyano groups, a group wherein one or more =CH— groups constituting the rings are substituted by nitrogen atoms or a group wherein one or more —CH$_2$— groups constituting the rings are substituted by oxygen atoms or sulfur atoms, include the following compounds. However, such a compound of the formula (1) is not limited to such specific examples.

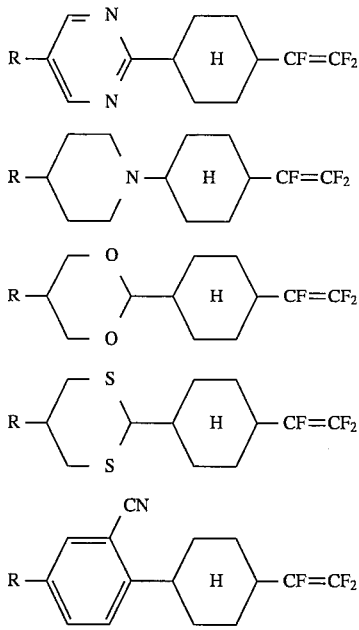

The compound of the formula (1) of the present invention can be prepared by a process which comprises fluorinating 1,1-difluoro-2-(trans-4-substituted cyclohexyl)ethylene of the formula (13), followed by dehydrofluorination. By this process, the compound of the present invention can efficiently be prepared while maintaining the stereochemistry of the cyclohexyl group.

Namely, the 1,1-difluoro-2-(trans-4-substituted cyclohexyl)ethylene of the formula (13) is fluorinated to obtain a compound of the formula (14). This fluorination reaction is conducted preferably by reacting the compound of the formula (13) with cobalt trifluoride in the presence of water. The amount of cobalt trifluoride is preferably from 2 to 15 equivalents, more preferably from 6 to 10 equivalents, per equivalent of the compound of the formula (13). Further, the amount of water is at a level of from 0.01 to 0.2 part by weight, preferably from 0.05 to 0.1 part by weight, per part by weight of the compound of the formula (13). The temperature for the fluorination reaction is usually at a level of from 20° to 120° C., preferably from 90° to 105° C. The time for the fluorination reaction is usually from about 0.5 to 6 hours, preferably from 1 to 4 hours.

Then, the compound of the formula (14) is dehydrofluorinated to obtain a compound of the formula (1) of the present invention. This dehydrofluorination reaction is preferably carried out in the presence of an alkyl lithium, particularly preferably in the presence of n—$C_4H_9Li$. The amount of the alkyl lithium is usually preferably from about 1 to 1.2 equivalents, particularly preferably from 1 to 1.05 equivalents, per equivalent of the compound of the formula (14). The reaction temperature is preferably from −100° to −40° C., particularly preferably from −80° to −60° C. Further, it is preferred to use a solvent for the dehydrofluorination reaction. As the solvent, an ether or a hydrocarbon is preferred. Particularly preferred is tetrahydrofuran, diethyl ether or hexane. The amount of the solvent is preferably from 10 to 20 parts by weight, per part by weight of the compound of the formula (14).

On the other hand, the compound of the formula (13) can be readily prepared in accordance with conventional methods. As an example, a method may be mentioned wherein it is prepared from a compound of the formula (10). The following scheme illustrates a route for preparing the compound of the formula (13) of the present invention from a compound of the formula (10), and a route for preparing a compound of the formula (1) of the present invention from the compound of the formula (13). In the following scheme, R, A, Cy and m have the same meanings as in the formula (1).

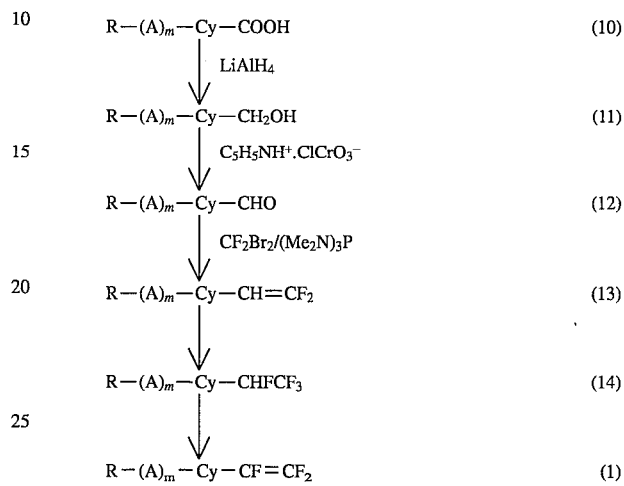

Firstly, a carboxylic acid derivative of the formula (10) is reduced by lithium aluminum hydride ($LiAlH_4$) to obtain an alcohol derivative of the formula (11). Then, this alcohol derivative (11) is oxidized by pyridinium chlorochromate to obtain an aldehyde derivative of the formula (12). Then, the obtained aldehyde derivative (12) is reacted with dibromodifluoromethane and trisdimethylaminophosphine to obtain a compound of the formula (13). Then, the compound of the formula (1) can be prepared from the compound of the formula (13) in accordance with the process of the present invention.

The compound of the formula (1) of the present invention is a novel compound. This compound is useful particularly as an intermediate for a liquid crystal compound. The liquid crystal compound which can be prepared from the compound of the formula (1) is not particularly limited. However, the following method may, for example, be mentioned for the preparation of a liquid crystal compound disclosed in Japanese Unexamined Patent Publication No. 40967/1994. In the following scheme, R, A, Cy and m have the same meanings as in the formula (1), and X is a bromine atom or an iodine atom, and $R^2$ is an alkyl group or a halogen atom.

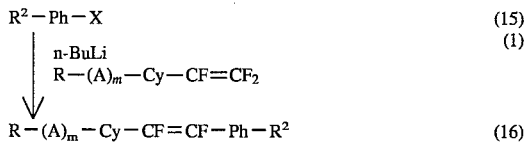

Firstly, a compound of the formula (15) is treated with n—$C_4H_9Li$ and then reacted with a compound of the formula (1) at a low temperature to obtain a compound of the formula (16).

In a case where a compound of the formula (18) which corresponds to the formula (16) wherein the —Ph—$R^2$ moiety is —Cy—$R^2$, is to be prepared, a halogenated cyclohexane compound of the formula (17) is lithium-modified by a Li metal in the presence of an electron transfer agent such as 4,4′-di-tert-butylbiphenyl and then reacted with a compound of the formula (1) at a low temperature to obtain a compound of the formula (18).

Such compounds of the formulas (16) and (18) are useful as compounds for STN or TFT, and they can readily be prepared in good yield by a simple operation by using the compound of the present invention as the starting material.

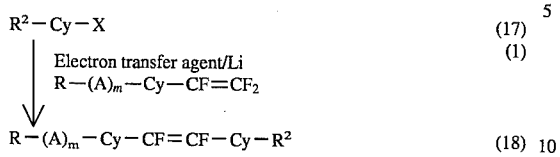

Now, the present invention will be described in further detail with reference to Examples. However, it should be understood that the present invention is by no means restricted by such specific Examples.

EXAMPLE 1

First Step

Into a 1 l four-necked flask, 22.3 g (0.588 mol) of LiAlH$_4$ and 300 cc of tetrahydrofuran (hereinafter referred to as THF) were introduced and cooled to 0° C. A solution having 100 g (0.588 mol) of trans-4-n-propylcyclohexane carboxylic acid dissolved in 300 cc of THF, was dropwise added thereto with stirring at a temperature of not higher than 10° C. over a period of 2 hours. The mixture was further stirred at room temperature for 12 hours. Then, 200 cc of a 20% sulfuric acid aqueous solution was added thereto, and the mixture was extracted with ethyl ether. The extract was washed with water and dried, and then the solvent was distilled off, followed by distillation under reduced pressure 88° C./4 mmHg) to obtain 89.3 g (yield: 97%) of trans-(1-hydroxymethyl-4-n-propyl)cyclohexane.

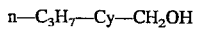

Second Step

Then, into a 2 l four-necked flask, 370.2 g (1.717 mols) of pyridinium chlorochromate, 23.5 g (0.286 mol) of sodium acetate and 1.2 l of methylene chloride were charged, and a methylene chloride solution containing 89.3 g (0.572 mol) of trans-(1-hydroxymethyl-4-n-propyl)cyclohexane obtained in the first step, was dropwise added thereto at room temperature. The mixture was stirred at room temperature for one hour. Then, 1 l of diethyl ether was added thereto, and anhydrous magnesium sulfate was further added thereto. The obtained tar-like substance was filtered off. The filtrate was concentrated under reduced pressure. Then, 200 cc of diethyl ether was again added thereto, and the tar-like substance was filtered off. The filtrate was concentrated under reduced pressure and then purified by silica gel column chromatography. The obtained crude solution was further distilled under reduced pressure (64° C./3 mmHg) to obtain 56.0 g (yield: 64%) of trans-(1-hydroxymethyl-4-n-propyl)cyclohexane carbaldehyde.

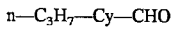

Third Step

Into a 1 l four-necked flask equipped with a condenser and a gas-supply tube, 400 cc of triglymedehydrated by CaH$_2$, was introduced and cooled to 0° C. Then, 101 g (0.481 mol) of dibromodifluoromethane (CF$_2$Br$_2$) was blown thereinto. Then, a solution containing 156.7 g (0.961 mol) of trisdimethylaminophosphine [(CH$_3$)$_2$N]$_3$P and 200 cc of triglyme, was dropwise added thereto at 0° C. over a period of 15 minutes. After the dropwise addition, the mixture was stirred at room temperature for 15 minutes. Then, a solution containing 37.0 g (0.24 mol) of 4-n-propyl-transcyclohexane carbaldehyde obtained in the second step and 100 cc of triglyme, was dropwise added thereto at room temperature over a period of 15 minutes, and the mixture was further reacted at 85° C. for 2 hours.

After cooling the mixture to 0° C., 300 cc of water was added thereto. The mixture was extracted with n-hexane, and the extract was washed with water and dried. Then, the solvent was distilled off, and the obtained crude solution was purified by silica gel column chromatography. The obtained crude solution was further distilled under reduced pressure (78° C./20 mmHg) to obtain 28.6 g (yield: 63%) of 2-(trans-4-n-propylcyclohexyl)-1,1-difluoroethylene.

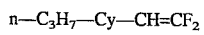

Fourth Step

Into a 2 l autoclave, 28.6 g (0.152 mol) of 2-(trans-4-n-propylcyclohexyl)-1,1-difluoroethylene obtained in the third step, 123.4 g (1.06 mols) of cobalt trifluoride, 1 cc of water and 1000 cc of CCl$_2$FCClF$_2$ (hereinafter referred to as FC-113) were charged and reacted at 100° C. for 3 hours. After cooling the mixture, inorganic salts were filtered off, and the organic layer was washed with a 10% NaHCO$_3$ aqueous solution and further with water. Then, the solvent was distilled off, and the obtained crude solution was purified by silica gel column chromatography to obtain 15.5 g (purity: 86%) of a crude solution of 2-(trans-4-n-propylcyclohexyl)-1,1,1,2-tetrafluoroethane.

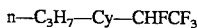

Fifth Step

Into a 1 l four-necked flask, 15.5 g of a crude solution of 2-(trans-4-n-propylcyclohexyl)-1,1,1,2-tetrafluoroethane obtained in the fourth step and 200 cc of dry THF were charged and cooled to –78° C. Then, 37.5 cc (0.06 mol) of a n-hexane solution of n—C$_4$H$_9$Li (1.6 mol/l) was dropwise added thereto over a period of 30 minutes. Then, the mixture was further reacted at –78° C. for 2 hours. Then, the temperature was raised to room temperature, and 500 cc of 1N hydrochloric acid was added thereto. The organic layer was separated. The aqueous layer was extracted with n-hexane, and the extract was combined with the organic layer. The combined organic layer was washed with water and dried. Then, the solvent was distilled off, and the obtained crude solution was purified by silica gel column chromatography to obtain 7.53 g (yield: 62%) of 2-(trans-4-n-propylcyclohexyl)-1,1,2-trifluoroethylene.

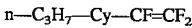

The spectrum data of this compound are shown below.

$^{19}$F—NMR(CDCl$_3$)δppm from CFCl$_3$:–107.4 ppm(d,d, J$_{F—F}$=92.8 Hz, J$_{F—F}$=33.1 Hz), –125.4 ppm (d,d,J$_{F—F}$=92.8 Hz, J$_{F—F}$=112.6 Hz), –182.7 ppm (d,d,d,J$_{F—F}$=33.1 Hz, J$_{F—F}$=112.6 Hz, J$_{F—H}$=26.5 Hz)

MS m/e: 206(M$^+$).

In the same manner as in Example 1, the following compounds were prepared.

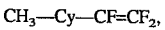

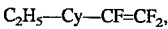

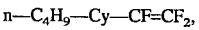

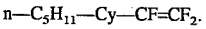

EXAMPLE 2

The reactions were carried out in the same manner as in Example 1 except that instead of trans-4-n-propylcyclohexane carboxylic acid used in the first step in Example, 148 g (0.588 mol) of trans-4-(trans-4-n-propylcyclohexyl)cyclohexane carboxylic acid was used, to obtain 9.50 g of 2-[trans-(4-n-propylcyclohexyl)cyclohexyl]-1,1,2-trifluoroethylene.

n—$C_3H_7$—Cy—Cy—CF=$CF_2$

MS m/e: 288($M^+$)

In the same manner as in Example 2, the following compounds were prepared.

$CH_3$—Cy—Cy—CF=$CF_2$, n—$C_2H_5$—Cy—Cy—CF=$CF_2$, n—$C_4H_9$—Cy—Cy—CF=$CF_2$, n—$C_5H_{11}$—Cy—Cy—CF=$CF_2$.

EXAMPLE 3

The reactions were carried out in the same manner as in Example 1 except that instead of trans-4-n-propylcyclohexane carboxylic acid used in the first step in Example 1, 101 g (0.588 mol) of trans-4-ethoxycyclohexane carboxylic acid was used, to obtain 7.10 g of 2-(trans-4-ethoxycyclohexyl)-1,1,2-trifluoroethylene.

$C_2H_5O$—Cy—CF=$CF_2$

MS m/e: 208($M^+$)

In the same manner as in Example 3, the following compounds were prepared.

$CH_3O$—Cy—CF=$CF_3$, n—$C_3H_7O$—Cy—CF=$CF_2$.

EXAMPLE 4

The reactions were carried out in the same manner as in Example 1 except that instead of trans-4-n-propylcyclohexane carboxylic acid used in the first step in Example 1, 115 g (0.588 mol) of trans-4-trifluoromethylcyclohexane carboxylic acid was used, to obtain 6.90 g of 2-(trans-4-trifluoromethylcyclohexyl)-1,1,2-trifluoroethylene.

$CF_3$—Cy—CF=$CF_2$

MS m/e: 232($M^+$)

In the same manner as in Example 4, the following compounds were prepared.

$C_2F_5$—Cy—CF=$CF_2$, $C_2F_5CH_2$—CY—CF=$CF_2$.

EXAMPLE 5

The reactions were carried out in the same manner as in Example 1 except that instead of trans-4-n-propylcyclohexane carboxylic acid used in the first step in Example 1, 95.6 g (0.588 mol) of trans-4-chlorocyclohexane carboxylic acid was used, to obtain 6.45 g of 2-(trans-4-chlorocyclohexyl)-1,1,2-trifluoroethylene.

Cl—Cy—CF=$CF_2$

MS m/e: 198($M^+$)

EXAMPLE 6

Into a 100 cc three-necked flask equipped with a reflux condenser, 0.13 g (0.0055 mol) of metal magnesium and 100 cc of dry THF were introduced under an argon atmosphere. Then, a few drops of 1-bromopropane were added thereto, and 0.67 g (0.0055 mol) of allyl bromide was dropwise added thereto at such a rate that heat generation continued. After completion of the dropwise addition, refluxing was continued for one hour. Then, the mixture was left to cool to room temperature.

Separately, into a 100 cc three-necked flask equipped with a reflux condenser, 20 cc of a dry THF solution containing 0.99 g (0.005 mol) of 2-(trans-4-chlorocyclohexyl)-1,1,2-trifluoroethylene obtained in Example 5 and 0.1 g of 1,3-bis(diphenylphosphino)propane dichloronickel [$NiCl_2$(dppp)], was introduced under an argon atmosphere, and the above solution was dropwise added thereto by means of a dropping funnel.

After the dropwise addition, the mixture was stirred at room temperature for further 24 hours. Then, 20 cc of water was added thereto. Further, 20 cc of 20% hydrochloric acid was added thereto. The organic layer was separated, washed with water and dried. Then, the solvent was distilled off. The obtained crude product was purified by silica gel column chromatography to obtain 0.56 g (yield: 55%) of 2-(trans-4-allylcyclohexyl)-1,1,2-trifluoroethylene.

$CH_2$=$CHCH_2$—Cy—CF=$CF_2$

MS m/e: 204($M^+$)

EXAMPLE 7

Into a 100 cc three-necked flask equipped with a reflux condenser, 0.13 g (0.0055 mol) of metal magnesium and 10 cc of dry THF were introduced under an argon atmosphere. Then, a few drops of 1-bromopropane were added thereto. Further, 0.99 g (0.005 mol) of 2-(trans-4-chlorocyclohexyl)-1,1,2-trifluoroethylene obtained in Example 5 was dropwise added thereto at such a rate that heat generation continued. After completion of the dropwise addition, refluxing was continued for one hour. Then, the mixture was left to cool to room temperature.

Separately, into a 100 cc three-necked flask equipped with a reflux condenser, 20 cc of a dry THF solution containing 0.65 g (0.0055 mol) of HC≡$CCH_2Br$ and 0.1 g of 1,3-bis(diphenylphosphino)propane dichloronickel [$NiCl_2$(dppp)] was introduced, and the above solution was dropwise added thereto by means of a dropping funnel.

After the dropwise addition, the mixture was further stirred at room temperature for 24 hours, and then 20 cc of water was added thereto. Further, 20 cc of 20% hydrochloric acid was added thereto. The organic layer was separated, washed with water and dried. Then, the solvent was distilled off. The obtained crude product was purified by silica gel column chromatography to obtain 0.53 g (yield: 52%) of 2-[trans-4-(2-propynyl)cyclohexyl]-1,1,2-trifluoroethylene.

HC≡$CCH_2$—Cy—CF=$CF_2$

MS m/e: 202($M^+$)

EXAMPLE 8

Into a 100 cc three-necked flask equipped with a reflux condenser, 0.13 g (0.0055 mol) of metal magnesium and 10 cc of dry THF were introduced under an argon atmosphere. Then, a few drops of 1-bromopropane were added thereto. Further, 0.99 g (0.005 mol) of 2-(trans-4-chlorocyclohexyl)-1,1,2-trifluoroethylene obtained in Example 5 was dropwise added thereto at such a rate that heat generation continued. After completion of the dropwise addition, refluxing was continued for one hour. Then, the mixture was left to cool to room temperature.

Separately, into a 100 cc three-necked flask equipped with a reflux condenser, 20 cc of a dry THF solution containing 1.35 g (0.0055 mol) of 4-n-propyliodobenzene and 0.1 g of 1,3-bis(diphenylphosphino)propane dichloronickel [NiCl$_2$(dppp)] was introduced under an argon atmosphere, and the above solution was dropwise added thereto by means of a dropping funnel.

Further, the mixture was stirred at room temperature for 24 hours, and then 20 cc of water was added. Further, 20 cc of 20% hydrochloric acid was added thereto. The organic layer was separated, washed with water and dried. Then, the solvent was distilled off. The obtained crude product was purified by silica gel column chromatography to obtain 0.86 g (yield: 61%) of 2-[trans-4-(4-n-propylphenyl)cyclohexyl]-1,1,2-trifluoroethylene.

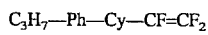

MS m/e: 282(M$^+$)

In the same manner as in Example 8, the following compounds were prepared.

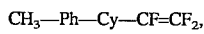

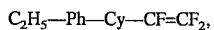

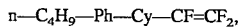

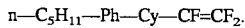

EXAMPLE 9

The reactions were carried out in the same manner as in Example 1 except that instead of trans-4-n-propylcyclohexane carboxylic acid used in the first step in Example 1, 85.8 g (0.588 mol) of trans-4-fluorocyclohexane carboxylic acid was used, to obtain 6.08 g of 2-(trans-4-fluorocyclohexyl)-1,1,2-trifluoroethylene.

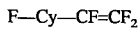

MS m/e: 182(M$^+$)

EXAMPLE 10

The reactions were carried out in the same manner as in Example 1 except that instead of trans-4-n-propylcyclohexane carboxylic acid used in the first step in Example 1, 117.6 g (0.588 mol) of trans-4-trifluoromethoxycyclohexane carboxylic acid was used, to obtain 7.12 g of 2-(trans-4-trifluoromethoxycyclohexyl)-1,1,2-trifluoroethylene.

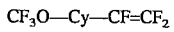

MS m/e: 248(M$^+$)

In the same manner as in Example 10, the following compounds were prepared.

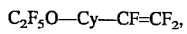

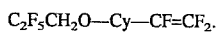

REFERENCE EXAMPLE 1

Into a 300 cc four-necked flask, 5.59 g (25.2 mmol) of 4-fluroiodobenzene and 30 cc of dry ethyl ether were charged and cooled to −78° C. Then, 17 cc (27.8 mmol) of a n-hexane solution of n—C$_4$H$_9$Li (1.63 mol/l) was dropwise added thereto over a period of 15 minutes. Further, the mixture was stirred at −78° C. for one hour. Then, 3.8 cc (25.5 mmol) of N,N,N',N'-tetramethylene ethylenediamine was added thereto. Further, a dry diethyl ether (10 cc) solution containing 1.3 g (6.31 mmol) of 2-(trans-4-n-propylcyclohexyl)-1,1,2-trifluoroethylene obtained in Example 1, was dropwise added thereto over a period of 30 minutes. Further, the mixture was reacted at the same temperature for one hour, and then stirred at room temperature for one hour. Then, 50 cc of 1N hydrochloric acid was added thereto. The organic layer was separated. The aqueous layer was extracted with n-hexane, and the extract was combined with the organic layer. The combined organic layer was washed with water and dried. Further, the solvent was distilled off. The obtained crude solution was purified by silica gel column chromatography to obtain a solid. This solid was recrystallized from methanol to obtain 0.71 g (yield: 40%) of (E)-1-(4-fluorophenyl)-2-(trans-4-n-propylcyclohexyl)-1,2-difluoroethylene.

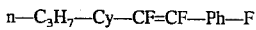

REFERENCE EXAMPLE 2

Into a 200 ml four-necked flask, 4.24 g (15.9 mmol) of 4,4'-di-t-butylbiphenyl and 50 ml of tetrahydrofuran (THF) were introduced and cooled to 0° C. Then, 0.22 g 31.8 mmol) of lithium metal and 0.01 g of bromine were added thereto under an argon atmosphere, and the mixture was stirred at the same temperature for 3 hours.

Then, after confirming that the reaction solution was dark blue, the mixture was cooled to −70° C. Then, a solution having 1.22 g (7.57 mmol) of 1-chloro-4-n-propylcyclohexane (cis-form/trans-form=2/1) dissolved in 10 ml of THF, was dropwise added with stirring at a temperature of not higher than −50° C. The mixture was further stirred at −70° C. for 30 minutes.

Then, a mixed solution containing 1.3 g (6.31 mmol) of 2-(trans-4-n-propylcyclohexyl)-1,1,2-trifluoroethylene obtained in Example 1 and 10 ml of dry THF, was dropwise added thereto at the same temperature over a period of 15 minutes. The mixture was reacted at the same temperature for one hour and then the temperature was raised to −10° C. Then, 100 ml of 1N hydrochloric acid was added thereto. The organic layer was separated. The aqueous layer was extracted with n-hexane, and the extract was combined with the organic layer. The combined organic layer was washed with water and dried. Then, the solvent was distilled off, and the obtained crude solution was purified by silica gel column chromatography. The obtained solid was further recrystallized from ethanol to obtain 1.18 g (yield: 60%) of (E)-1,2-bis(trans-4-n-propylcyclohexyl)-1,2-difluoroethylene.

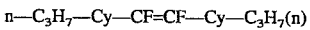

REFERENCE EXAMPLE 3

To 80 wt. % of a liquid crystal composition (ZLI-1565, tradename) manufactured by Merck, 20 wt. % of the compound prepared in Reference Example 1 i.e. (E)-1-(4-fluoro phenyl)-2-(trans-4-n-propylcyclohexyl)-1,2difluoroethylene, was added, to obtain a liquid crystal composition (a).

Separately, to 80 wt. % of a liquid crystal composition (ZLI-1565, tradename) manufactured by Merck, 20 wt. % of the compound prepared in Reference Example 2 i.e. (E)-1,2-bis(trans-4-n-propylcyclohexyl)-1,2-difluoroethylene, was added, to obtain a liquid crystal composition (b).

The obtained liquid crystal compositions (a) and (b) and the liquid crystal composition (c) manufactured by Merck had the following liquid crystal properties.

TABLE 1

| Liquid crystal properties | Liquid crystal Composition (a) | Liquid crystal Composition (b) | Liquid crystal Composition (c) |
| --- | --- | --- | --- |
| Clearing point (Tc) | 74.1° C. | 78.0° C. | 86.4° C. |
| Δn | 0.123 | 0.115 | 0.123 |
| Viscosity/25° C. | 11.5 cSt | 13.2 cSt | 15.4 cSt |
| Viscosity/0° C. | 46.4 cSt | — | 59.2 cSt |

What is claimed is:

1. A 1,1,2-trifluoro-2-(trans-4-substituted cyclohexyl)ethylene of the formula (1):

$$R-(A)_m-Cy-CF=CF_2 \quad (1)$$

wherein R is a halogen atom, a cyano group, a $C_{1-10}$ alkyl group, a $C_{1-10}$ alkyl group wherein at least one hydrogen atom is replaced with a fluorine atom, a $C_{1-10}$ alkoxyl group, a $C_{1-10}$ alkoxyl group wherein at least one hydrogen atom is replaced with a fluorine atom, a $C_{1-10}$ alkenyl group containing at least one carbon-carbon double bond, a $C_{1-10}$ alkenyl group containing at least one carbon-carbon double bond and wherein at least one hydrogen atom is replaced with a fluorine atom, a $C_{1-10}$ alkynyl group containing at least one carbon-carbon triple bond, a $C_{1-10}$ alkynyl group containing at least one carbon-carbon triple bond and wherein at least one hydrogen atom is replaced with a fluorine atom, a $C_{1-10}$ alkyl group containing therein one carbonyl group, or a $C_{1-10}$ alkyl group containing therein one carbonyl group and wherein at least one hydrogen atom is replaced with a fluorine atom;

Cy is an unsubstituted trans-1,4-cyclohexylene group;

A is a trans-1,4-cyclohexylene group, a trans-1,4-cyclohexylene group substituted with at least one halogen atom or cyano group, a trans-1,4-cyclohexylene group wherein at least one —CH₂— group is replaced by an oxygen or sulfur atom, a trans-1,4-cyclohexylene group wherein at least one =CH— group is replaced by a nitrogen atom, a trans-1,4cyclohexylene group substituted with at least one halogen atom or cyano group and wherein at least one —CH₂— group is replaced with an oxygen or sulfur atom, a trans-1,4-cyclohexylene group substituted with at least one halogen atom or cyano group and wherein at least one =CH— group is replaced by a nitrogen atom, a 1,4-phenylene group, a 1,4-phenylene group substituted with at least one halogen atom or cyano group, a 1,4-phenylene group wherein at least one =C— group is replaced with a nitrogen atom, a 1,4-phenylene group substituted with at least one halogen atom or cyano group and wherein at least one =C— group is replaced with a nitrogen atom, a 1,4-cyclohexenylene group, a 1,4-cyclohexenylene group substituted with at least one halogen atom or cyano group, a 1,4-cyclohexenylene group wherein at least one —CH₂— group is replaced with an oxygen or sulfur atom, a 1,4-cyclohexenylene group wherein at least one =CH— group is replaced with a nitrogen atom, a 1,4-cyclohexenylene group substituted with at least one halogen atom or cyano group and wherein at least one —CH₂— group is replaced with an oxygen or sulfur atom, or a 1,4-cyclohexenylene group substituted with at least one halogen atom or cyano group and wherein at least one =CH— group is replaced with a nitrogen atom; and m is 0 or 1.

2. A 1,1,2-trifluoro-2-(trans-4-substituted cyclohexyl)ethylene of the formula (2):

$$R^1-(A^1)_m-Cy-CF=CF_2 \quad (2)$$

wherein $R^1$ is a $C_{1-10}$ alkyl group, a $C_{1-10}$ alkyl group wherein at least one hydrogen atom is replaced with a fluorine atom, a $C_{1-10}$ alkoxyl group, a $C_{1-10}$ alkoxyl group wherein at least one hydrogen atom is replaced with a fluorine atom, a $C_{1-10}$ alkenyl group containing at least one carbon-carbon double bond, a $C_{1-10}$ alkenyl group containing at least one carbon-carbon double bond and wherein at least one hydrogen atom is replaced with a fluorine atom, a $C_{1-10}$ alkynyl group containing at least one carbon-carbon triple bond, a $C_{1-10}$ alkynyl group containing at least one carbon-carbon triple bond and wherein at least one hydrogen atom is replaced with a fluorine atom, a $C_{1-10}$ alkyl group containing therein one carbonyl group, or a $C_{1-10}$ alkyl group containing therein one carbonyl group and wherein at least one hydrogen atom is replaced with a fluorine atom;

Cy is an unsubstituted trans-1,4-cyclohexylene group;

$A^1$ is a trans-1,4-cyclohexylene group, a 1,4-phenylene group or a 1,4-cyclohexenylene group, wherein each of such cyclic groups is unsubstituted or substituted by one or more fluorine atoms; and m is 0 or 1.

3. The 1,1,2-trifluoro-2-(trans-4-substituted cyclohexyl)ethylene according to claim 2, wherein m is 0.

4. The 1,1,2-trifluoro-2-(trans-4-substituted cyclohexyl)ethylene according to claim 2, wherein m is 1, and $A^1$ is an unsubstituted trans-1,4-cyclohexylene group, an unsubstituted 1,4-phenylene group, a 1,4-phenylene group having one or two fluorine atoms, or an unsubstituted 1,4-cyclohexenylene group.

5. The 1,1,2-trifluoro-2-(trans-4-substituted cyclohexyl)ethylene according to claim 2, wherein m is 1, and $A^1$ is an unsubstituted trans-1,4-cyclohexylene group.

6. The 1,1,2-trifluoro-2-(trans-4-substituted cyclohexyl)ethylene according to claim 2, wherein $R^1$ is of a straight chain structure.

7. A process for producing a 1,1,2-trifluoro-2-(trans-4-substituted cyclohexyl)ethylene of the formula (1), which comprises fluorinating a compound of the formula (13) to obtain a compound of the formula (14), and further dehydrofluorinating the compound of the formula (14):

$$R-(A)_m-Cy-CH=CF_2 \quad (13)$$

$$R-(A)_m-Cy-CHFCF_3 \quad (14)$$

$$R-(A)_m-Cy-CF=CF_2 \quad (1)$$

wherein R is a halogen atom, a cyano group, a $C_{1-10}$ alkyl group, a $C_{1-10}$ alkyl group wherein at least one hydrogen atom is replaced with a fluorine atom, a $C_{1-10}$ alkoxyl group, a $C_{1-10}$ alkoxyl group wherein at least one hydrogen atom is replaced with a fluorine atom, a $C_{1-4}$ alkenyl group containing at least one carbon-carbon double bond, a $C_{1-10}$ alkenyl group containing at least one carbon-carbon double bond and wherein at least one hydrogen atom is replaced with a fluorine atom, a $C_{1-10}$ alkynyl group containing at least one carbon-carbon triple bond, a $C_{1-10}$ alkynyl group containing at least one carbon-carbon triple bond and wherein at least one hydrogen atom is replaced with a fluorine atom, a $C_{1-10}$ alkyl group containing therein one carbonyl group, or a $C_{1-10}$ alkyl group containing therein one carbonyl group and wherein at least one hydrogen atom is replaced with a fluorine atom;

Cy is an unsubstituted trans-1,4-cyclohexylene group;

A is a trans-1,4-cyclohexylene group, a a trans-1,4-cyclohexylene group substituted with at least one halogen atom or cyano group, a trans-1,4-cyclohexylene group wherein at least one —CH$_2$— group is replaced by an oxygen or sulfur atom, a trans-1,4-cyclohexylene group wherein at least one =CH— group is replaced by a nitrogen atom, a trans-1,4,-cyclohexylene group substituted with at least one halogen atom or cyano group and wherein at least one —CH$_2$— group is replaced with an oxygen or sulfur atom, a 1,4-phenylene group, a trans-1,4-cyclohexylene group substituted with at least one halogen atom or cyano group and wherein at least one =CH— group is replaced with a nitrogen atom, a 1,4,-phenylene group, a 1,4-phenylene group substituted with at least one halogen atom or cyano group, a 1,4-phenylene group wherein at least one =C— group is replaced with a nitrogen atom, a 1,4-phenylene group substituted with at least one halogen atom or cyano group and wherein at least one =C— group is replaced with a nitrogen atom, a 1,4-cyclohexenylene group, a 1,4-cyclohexenylene group substituted with at least one halogen atom or cyano group, a 1,4-cyclohexenylene group wherein at least one —CH$_2$— group is replaced with an oxygen or sulfur atom, a 1,4-cyclohexenylene group wherein at least one =CH— group is replaced with a nitrogen atom, a 1,4-cyclohexenylene group substituted with at least one halogen atom or cyano group and wherein at least one —CH$_2$— group is replaced with an oxygen or sulfur atom, or a 1,4-cyclohexenylene group substituted with at least one halogen atom or cyano group and wherein at least one =CH— is replaced with a nitrogen atom; and m is 0 or 1.

8. The process according to claim 7, wherein the fluorination is carried out by reacting the compound of the formula (13) with cobalt trifluoride in the presence of water.

9. The process according to claim 7, wherein the dehydrofluorination is carried out in the presence of an alkyl lithium.

10. The process according to claim 8, wherein the dehydrofluorination is carried out in the presence of an alkyl lithium.

* * * * *